United States Patent
Torregrossa et al.

(10) Patent No.: US 10,711,030 B2
(45) Date of Patent: Jul. 14, 2020

(54) PROCESS FOR THE PREPARATION OF ALLOPREGNANOLONE

(71) Applicant: Farmabios S.p.A., Gropello Cairoli (IT)

(72) Inventors: Enrico Torregrossa, Trapani (IT); Marco Brusasca, Valenza (IT); Cristina Manfrotto, Gropello Cairoli (IT)

(73) Assignee: FARMABIOS S.P.S., Gropello Cairoli (PV) (IT)

( * ) Notice: Subject to any disclaimer, the term of this patent is extended or adjusted under 35 U.S.C. 154(b) by 0 days.

(21) Appl. No.: 16/527,183

(22) Filed: Jul. 31, 2019

(65) Prior Publication Data

US 2020/0087341 A1   Mar. 19, 2020

(30) Foreign Application Priority Data

Sep. 18, 2018  (IT) .................. 102018000008664

(51) Int. Cl.
*C08J 7/00* (2006.01)
*C07J 7/00* (2006.01)

(52) U.S. Cl.
CPC ........... *C07J 7/002* (2013.01); *C07B 2200/13* (2013.01)

(58) Field of Classification Search
CPC .............................. C07J 7/002; C07B 2200/13
See application file for complete search history.

(56) References Cited

U.S. PATENT DOCUMENTS 3,013,031 A * 12/1961 Cutler, Jr. ................. C07J 5/00
552/591

FOREIGN PATENT DOCUMENTS

WO   2009108804 A2   9/2009

OTHER PUBLICATIONS

Varasi et al, Journal of Organic Chemistry, A Revised Mechanism for the Mitsunobu Reaction, 1987, 52, pp. 4235-4238. (Year: 1987).*
Purdy et al., "Synthesis, Metabolism, and Pharmacological Activity of 3Alpha-Hydroxy Steroids Which Potentiate Gaba-Receptor-Mediated Chloride Ion Uptake in Rat Cerebral Cortical Synaptoneurosomes", Journal of Medicinal Chemistry, 1990, vol. 33, No. 6, pp. 1572-1581.
Euw et al., "3.alpha.,17.alpha.,21-Trihydroxy-5.alpha.-pregnan-20-one und Subst. TR 1018", Helvetica Chimica Acta 1962, vol. 45, No. 1, pp. 224-232.
Lieberman et al., "Studies in Steroid Metabolism II. Identification and Characterization of Ketosteroids Isolated From Urine of Healthy and Diseased Persons", Journal of Biological Chemistry, 1948, vol. 172, No. 1, pp. 263-295.
Kapras et al., "Preparation of steroid sulfamates and their interaction with GABAA receptor", Collection Symposium Series (XIIITH Symposium on Chemistry of Nucleic Acid Components Spindleruv Mlyn, 2005, vol. 74, No. 4, pp. 643-650.
Marker, "Sterols. CVIII. The Preparation of Dihydroandrosterone and Related Compounds from Diosgenin and Tigogenin", Journal of the American Chemical Society, 1940, vol. 62, No. 10, pp. 2621-2625.
Search Report for Corresponding Italian Application No. 201800008664, (10 Pages) (dated Jun. 12, 2019).
Van Den Heuvel et al., "Gas-chromatographic behavior of trifluoracetoxy steroids", Biochim. Biophys. Acta 48, 1961, pp. 596-599.
"[621] Chromatography", Physical Tests, First Supplement to USP 40—NF 35, pp. 1-12.
Chromacademy; "The Theory of HPLC, Quantitative arid Qualitative HPLC"; Crawford Scientific, pp. 1-24.

* cited by examiner

*Primary Examiner* — Paul A Zucker
(74) *Attorney, Agent, or Firm* — Lucas & Mercanti, LLP

(57) ABSTRACT

A method for the purification of allopregnanolone is disclosed. Allopregnanolone prepared from isopregnanolone contains impurities such as triphenylphosphine oxide and other unknown impurities. To remove these impurities and purify allopregnanolone, the allopregananolone is dissolved in acetonitrile, and crystallized from the acetonitrile. The resulting crystallized allopregnanolone may then be re-crystallized from acetonitrile to further purify the allopregnanolone.

13 Claims, 8 Drawing Sheets

PROCESS FOR THE PREPARATION OF ALLOPREGNANOLONE

CROSS-REFERENCE TO RELATED APPLICATIONS

This application claims the benefit of Italian Patent Application No. 102018000008664, filed Sep. 18, 2018, the contents of which are incorporated herein by reference.

FIELD OF INVENTION

The present invention relates to a process for the preparation of allopregnanolone, more particularly for the preparation of allopregnanolone with a high degree of purity.

Allopregnanolone is an endogenous neurosteroid of formula (I):

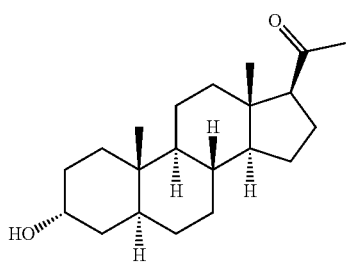

(I)

with chemical name 1-(3-hydroxy-10,13-dimethyl-2,3,4,5,6,7,8,9,11,12,14,15,16,17-tetradecahydro-1H-ciclopenta[a]fenantren-17-yl)ethanone.

Allopregnanolone is a positive allosteric modulator of the activity of γ-aminobutyric acid (GABA) on the ionotropic receptor $GABA_A$. Furthermore, it also acts as an inhibitor of L-type voltage-gated calcium channels (L-VGCCs).

Presently, allopregnanolone is under study for the treatment of different pathologies such as, for example, epilepsy, postpartum depression and post-traumatic stress disease (PTSD).

BACKGROUND OF THE INVENTION

Several processes for the preparation of allopregnanolone are known in the literature. The conversion of 3β-hydroxy-5α-pregnan-20-one (isopregnanolone) into 3α-hydroxy-5α-pregnan-20-one (allopregnanolone) through Mitsunobu reaction and subsequent basic hydrolysis is described, for example, in *J. Med. Chem.* 1990, 33, 1572-1581. However, the resultant product must undergo a laborious purification phase consisting of crystallization from ethyl acetate/aqueous ethanol, column chromatography with 2% acetone in dichloromethane and, finally, crystallization from aqueous ethanol.

International patent application WO 2009/108804 describes a process consisting of the catalytic hydrogenation of pregnenolone to give isopregnanolone, purified by crystallization from hexane/ethyl acetate, which is then subjected to Mitsunobu reaction and hydrolysis to yield allopregnanolone, purified by column chromatography with ethyl acetate in hexane (0-35%).

Finally, in *Collect. Czech. Chem. Commun.* 2009, 74, 643-650, the conversion of isopregnanolone into the formic ester of allopregnanolone through Mitsunobu reaction is described. The resultant ester intermediate is subjected to column chromatography in petroleum ether/acetone (98:2) and, subsequently, to crystallization from acetone. After basic hydrolysis, allopregnanolone is purified by crystallization from acetone/ethyl acetate.

All the processes known in the art foresee a laborious purification phase which includes the use of at least one chromatography and/or chromatography followed by crystallization. Furthermore, the purification of allopregnanolone according to the crystallizations known in the art does not allow to efficaciously remove impurities and reaction byproducts.

However, since the product is for the use in therapy, a process which allows to obtain allopregnanolone with a purity of pharmaceutical grade and, at the same time, which is of easy industrial applicability is required.

Therefore, there is still the need of an improved process for the preparation of allopregnanolone which overcomes all the drawbacks of the known processes. In particular, there is the need of an improved method for the purification of allopregnanolone, for example, a method which does not foresee any laborious multistep purification and/or the use of chromatography, which is not time consuming, expensive and disadvantageous with respect to the yield.

SUMMARY OF THE INVENTION

A first object of the present invention is a method for the purification of allopregnanolone comprising the crystallization of allopregnanolone from acetonitrile.

It is another object of the present invention a process for the preparation of allopregnanolone which is carried out through the formation, and the subsequent purification, of 3α-trifluoroacetoxy-5α-pregnan-20-one (herein after also referred to as allopregnanolone 3α-trifluoroacetate).

Allopregnanolone 3α-trifluoroacetate is another object of the invention.

Definitions

All the terms used in the present description, unless otherwise indicated, are to be understood in their common meaning as known in the art.

The expression "purity of pharmaceutical grade", within the scope of the present invention, means that the product has a purity to be suitable for the use as a medicament.

The annotation "V" preceded by a number, means how many times, in terms of volume, the amount of a substance exceeds the given amount of another substance. For example, given 7.5 g of allopregnanolone 3α-trifluoroacetate, add 10V of methanol means to add 75 mL of methanol.

The term "about" comprises the range of experimental error which may occur in a measurement. In particular, when referred to a value, it means the given value plus or minus 5% and, when referred to a range, it means the outer values plus or minus 5%.

DETAILED DESCRIPTION OF THE INVENTION

Figure 1:
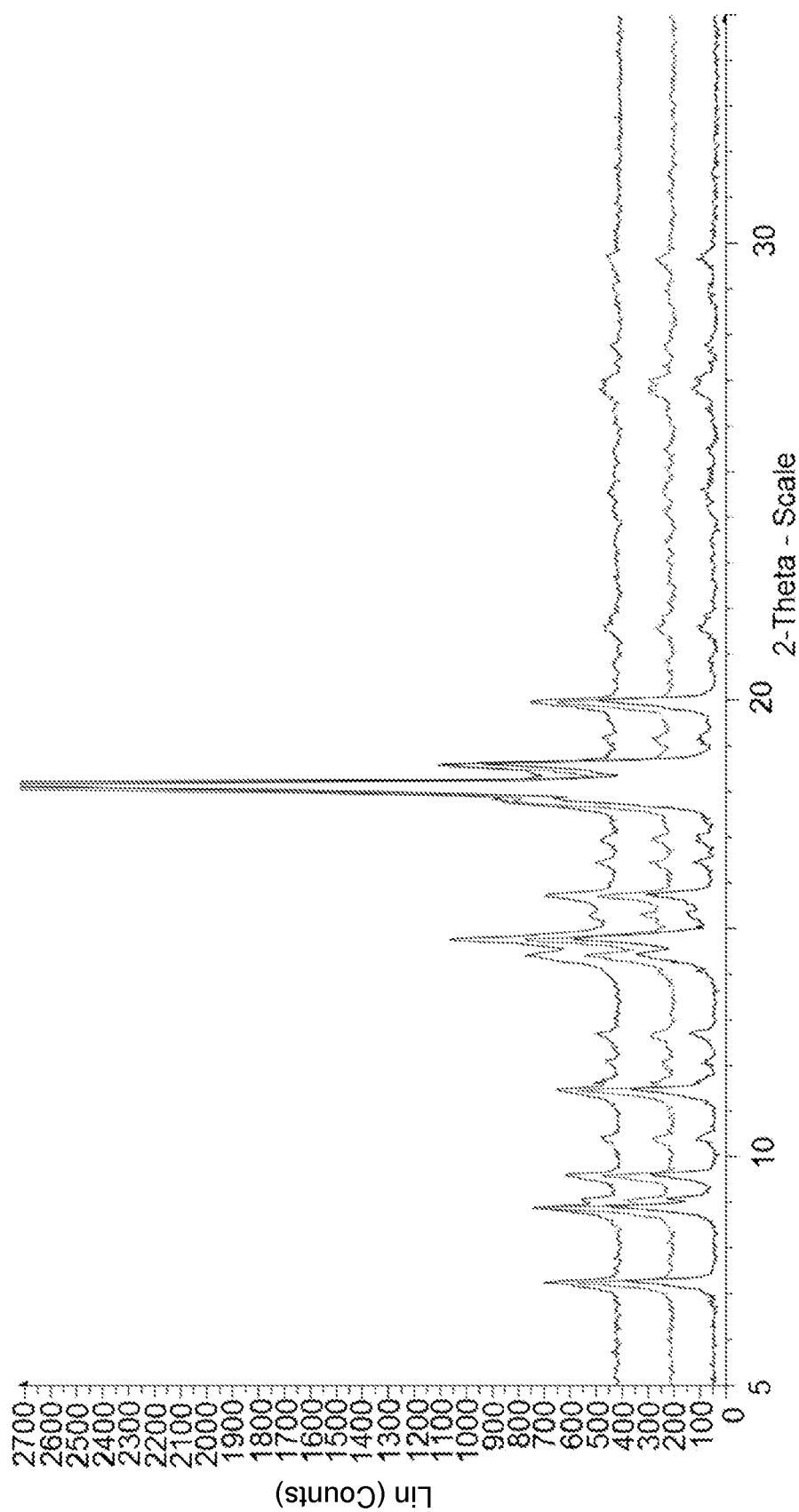
FIG. 1: XRPD spectrum of allopregnanolone obtained according to the invention.
Figure 2:
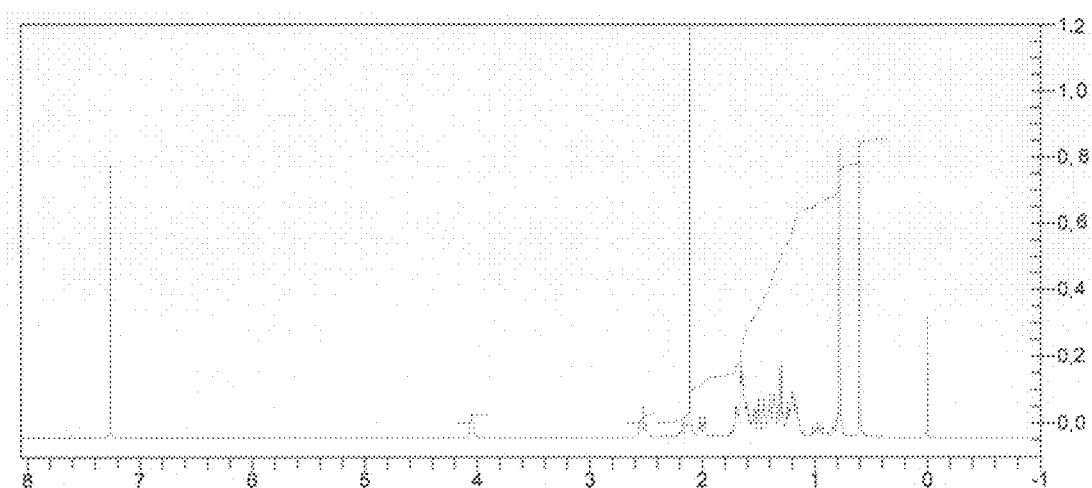
FIG. 2: $^1H$ NMR spectrum of allopregnanolone obtained according to the invention.
Figure 3:
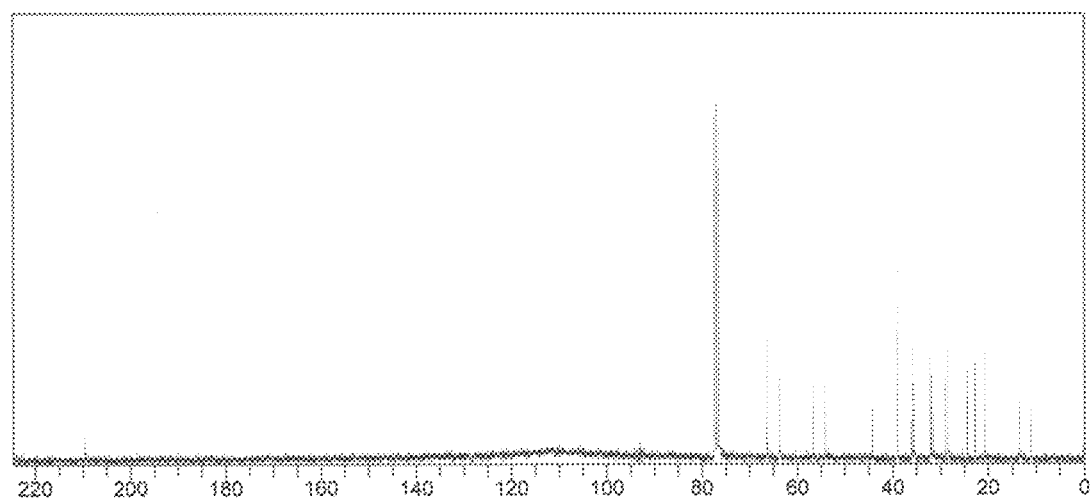
FIG. 3: $^{13}C$ NMR spectrum of allopregnanolone obtained according to the invention.

Starting from isopregnanolone and following the process described in WO 2009/108804 it was possible to isolate allopregnanolone. However, the chromatography as final purification step does not allow to apply the process on industrial scale. Furthermore, the isolated product shows a content in triphenylphosphine oxide (TPPO), as well as in other unknown impurities, in amounts much higher than the permitted ICH limit of 0.10% (Table 1).

TABLE 1

| Isopregnanolone (g) | Allopregnanolone purity(%) | TPPO (% A) | Yield (%) |
| --- | --- | --- | --- |
| 1.59 | 78 | 16.9 | 75 | wherein % A (or area %) refers to the percent concentration of the compound with respect to the total in the injected solution and it is obtained by the following formula:

$A \% = [\text{Area under the peak curve (signal of interest)} / \text{sum of the total areas}]\%$ TPPO, a byproduct of the Mitsunobu reaction derived from the oxidation of triphenylphosphine, is a potentially toxic impurity which can significantly affect the quality and the safety of the final product. In fact, in order to purify the product (allopregnanolone) or precursors thereof such as, for example, its 3-formyl derivative, and to remove the byproducts of the Mitsunobu reaction, including TPPO, the processes known in the literature always use chromatography.

In an attempt to obtain allopregnanolone in compliance with the ICH specifications (that is unknown impurities ≤0.10% and known impurities ≤0.15% based on HPLC analysis) without using chromatographic techniques, the inventors of the present invention have carried out several crystallization experiments with solvents or mixtures of solvents known in the literature such as, for example, aqueous ethanol, acetone/ethyl acetate, hexane/ethyl acetate, ethyl acetate/ethanol etc. (see Example 1). However, some impurities, particularly TPPO, proved to be difficult to remove. It should be noted that, in the experiments carried out with said solvents or mixtures of solvents (experiments B-E, Example 1), even the subsequent recrystallization from the same or from another solvent did not allow to increase the purity of the final product.

After extensive experimentation, the inventors have surprisingly found that the crystallization of allopregnanolone from acetonitrile allows to obtain the final product in compliance with the ICH specifications and then substantially free (<<0.10% A; <<<0.10% w/w) of TPPO.

Therefore, a first object of the present invention is a method for the purification of allopregnanolone comprising the crystallization of allopregnanolone from acetonitrile.

Said purification can be carried out according to methods known in the art, in particular, by hot-cold crystallization wherein allopregnanolone is first dissolved at warm in acetonitrile to make ease and faster the dissolution, and then the resulting solution is cooled to achieve the product precipitation.

In an embodiment, the method for the purification of allopregnanolone of the present invention comprises:
  the dissolution of allopregnanolone in acetonitrile at warm;
  the cooling of the solution; and
  the separation of the precipitate.

In particular, allopregnanolone is dissolved in about 5-20V, preferably about 10V, acetonitrile and the resultant mixture is heated at a temperature between 70° C. and 90° C., preferably between 75±5° C. and 85°±5° C., more preferably at about 80° C. During the heating, the mixture can be kept under stirring, for example, for about 15±5 minutes or, if needed, for 30±5 minutes up to complete dissolution of the product.

The solution is then left to cool preferably at a temperature between −2° C. and 25° C., more preferably at 0°±2° C., thereby achieving the precipitation of allopregnanolone crystals. During the cooling, the mixture can be kept under stirring for a time sufficient to ensure the formation of allopregnanolone crystals. In an embodiment, the solution is kept under stirring for about 30±5 minutes.

The separation of the allopregnanolone crystals, obtained according to the process of the present invention, can be carried out according to any method known in the art, including, but not limited to, filtration under vacuum, gravity filtration, distillation, centrifugation, slow evaporation and the like. In a preferred embodiment, allopregnanolone is isolated by filtration under vacuum. The crystalline solid is washed with about 1V cold acetonitrile (5°±2° C.) and dried at a temperature between 30° C. and 50° C., preferably at about 45° C., for a suitable time period in order to bring the residual solvents below the ICH limits. A suitable time period can be, for example, between 10 and 20 hours, preferably about 16 hours. The drying can be carried out according to methods known in the art including, but not limited to, vacuum oven, Rotavapor®, air drying chamber, static bed dryer, fluid bed dryer, spray dryer and the like. Preferably, the drying is made by static bed drying under vacuum at 45°±5° C.

In a preferred embodiment, the crystallization of allopregnanolone can be followed by a re-crystallization from the same or a different solvent. Preferably, the re-crystallization is carried out from acetonitrile under the same conditions above reported.

In a particularly preferred embodiment, the process for the purification of allopregnanolone, according to the present invention, comprises:
  the dissolution of allopregnanolone in acetonitrile at a temperature of about 85° C.±5° C. keeping under stirring for about 15 minutes;
  the cooling of the solution at about 0° C. keeping under stirring for about 30 minutes;
  the separation of the precipitate by filtration under vacuum;
  the washing of the precipitate with acetonitrile;
  the drying under vacuum at a temperature of about 40° C. for about 16 hours; and, optionally,
  the re-crystallization of the precipitate from acetonitrile.

It should be also noted that the process of the present invention allows to obtain allopregnanolone with purity of pharmaceutical grade and also in crystalline form (herein also referred to as Form X).

Allopregnanolone, obtained according to the present invention, has been characterized by X-ray powder diffractometry (XRPD) and its TPPO content has been determined by high performance liquid chromatography (HPLC).

More particularly, allopregnanolone obtained according to the present invention shows, in the XRPD diffractogram (FIG. 1), at least three of the following characterizing peaks: 7.25, 8.87, 9.58, 11.43, 14.41, 14.77, 15.73, 17.78, 18.16, 18.60 and 19.98±0.2 degrees 2–θ.

Figure 4:
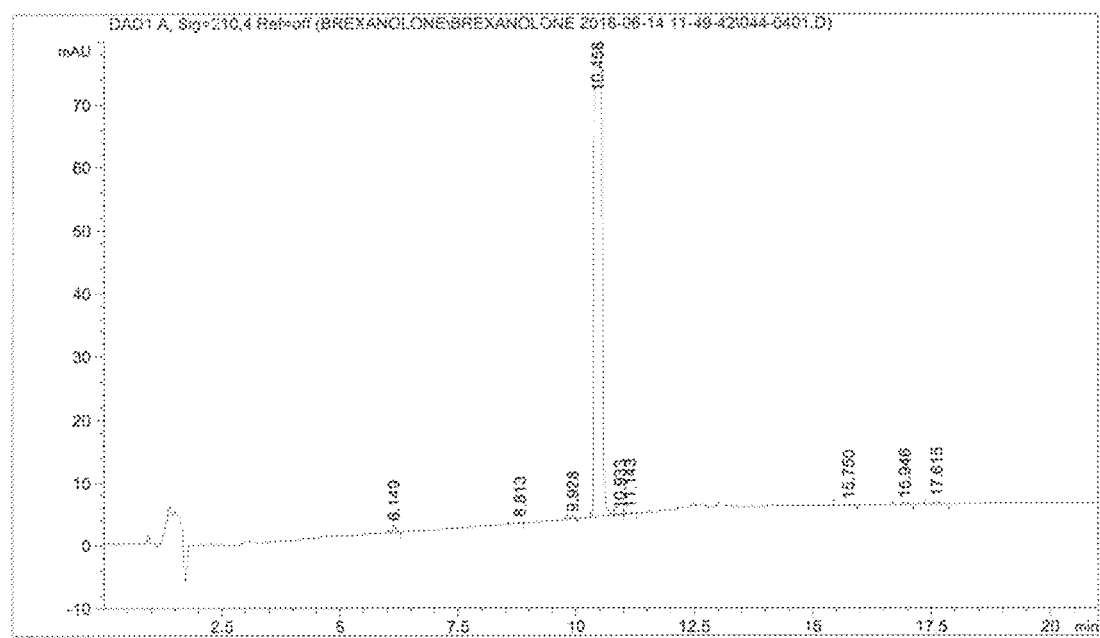
FIG. 4: HPLC chromatogram of allopregnanolone obtained according to the invention.

The HPLC chromatogram (FIG. 4) shows that allopregnanolone, obtained according to the present invention, has much less than 0.10% TPPO (retention time related to allopregnanolone rRT=about 0.59).

Notwithstanding the invention has been described in detail, it should be noted that the only essential feature of the present method for the purification of allopregnanolone is the crystallization solvent, that is acetonitrile.

For example, it has been observed that, even changing the duration of the hot/cold cycles, allopregnanolone is obtained according to the desired specifications.

Only the use of acetonitrile to give allopregnanolone in crystalline form X allowed to develop an improved process for the purification of allopregnanolone.

Without being bound to any specific theory, the inventors of the present invention believe that this surprising result is due to the peculiar solubility properties of both allopregnanolone and TPPO in acetonitrile. In fact, the product crystallizes from acetonitrile with high yield and complete removal of triphenylphosphine oxide which remains in solution also after the cooling of the solution. It should be noted that no solvents or mixtures of solvents which are known in the literature are able to achieve this dual function.

Allopregnanolone can be obtained by any method known in the art.

However, in an attempt to further increase the purity of the final product, the inventors have also developed a process for the preparation of allopregnanolone.

Therefore, a further object of the present invention is a method for the purification of allopregnanolone further comprising the preparation of allopregnanolone by Mitsunobu reaction of a compound of formula

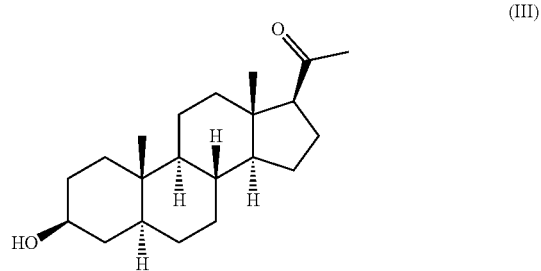

(III)

to give a compound of formula

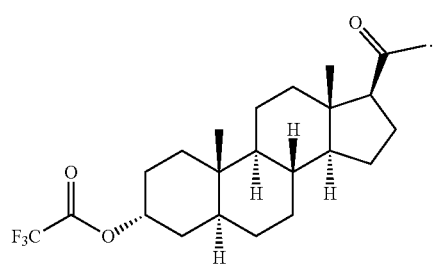

(II)

In particular, isopregnanolone (III) is reacted with trifluoroacetic acid in the presence of an azodicarboxylate, triphenylphosphine and sodium benzoate in a suitable reaction solvent, preferably tetrahydrofuran.

The azodicarboxylate can be selected from the group consisting of diethylazodicarboxylate (DEAD), diisopropylazodicarboxylate (DIAD) and di-tert-butyl azodicarboxylate (DBAD) and is preferably DEAD solid or dissolved in a suitable solvent, in particular toluene.

The intermediate compound of formula (II), that is allopregnanolone 3α-trifluoroacetate or 3α-trifluoroacetoxy-5α-pregnan-20-one, is a further object of the present invention.

It should be noted that the conversion of 3α-hydroxy-5α-pregnan-20-one into 3β-trifluoroacetoxy-5α-pregnan-2β-one through Mitsunobu reaction is known in the literature (Varasi et al. "A Revised Mechanism for the Mitsunobu Reaction"). However, the C3 of the resultant compound has inverted configuration with respect to the intermediate of the present invention and it is anyway isolated and purified by chromatography.

After extensive experimentation, the inventors of the present invention have found that the isolation and purification of allopregnanolone 3α-trifluoroacetate by filtration of a solution of the compound of formula (II) in diisopropyl ether (DIPE) followed by re-crystallization from isopropyl alcohol (IPA) can advantageously influence the purity of the final product, allopregnanolone.

Therefore, a further object of the present invention is a method for the purification of allopregnanolone comprising the filtration of a solution of the compound of formula (II) in diisopropyl ether and its re-crystallization from isopropyl alcohol.

In particular, allopregnanolone 3α-trifluoroacetate (II) is dissolved in about 2-10V, preferably about 6V, diisopropyl ether. To promote the dissolution, the mixture can be kept under stirring for a suitable period of time, for example, for about 30 minutes, until a precipitate (TPPO) is obtained. The solid precipitate is removed according to filtration techniques known in the art such as, for example, gravity filtration and filtration under vacuum. The filtrate, that is the solution of allopregnanolone 3α-trifluoroacetate in diisopropyl ether, is concentrated and then recovered with about 2-10V, preferably about 6V, isopropyl alcohol.

The resultant mixture is heated at a temperature between 60° C. and 90° C., preferably between 70° C. and 80° C., more preferably at about 75° C. While heating, the mixture can be kept under stirring, for example, for about 15±5 minutes or, if needed, for 30±5 minutes up to complete dissolution of the product.

The solution is then left cooling preferably at a temperature between −2° C. and 25° C., more preferably at 0° C., in order to obtain the precipitation of allopregnanolone 3α-trifluoroacetate crystals. While cooling, the mixture can be kept under stirring for enough time to ensure the formation of allopregnanolone 3α-trifluoroacetate crystals. In one embodiment, the solution is kept under stirring for about 30±5 minutes.

The separation of the allopregnanolone 3α-fluoroacetate crystals obtained according to the process of the present invention can be made according to any of the methods known in the art including, but not limited to, filtration under vacuum, gravity filtration, distillation, centrifugation, slow evaporation and the like. In a preferred embodiment, allopregnanolone 3α-trifluoroacetate is isolated by filtration under vacuum. The crystalline solid is washed with about 1V cold isopropyl alcohol (5°±2° C.) and dried at a temperature from 30° C. to 50° C., preferably at about 20-25° C., for a suitable period of time. The drying can be made according to methods known in the art including, but not limited to, vacuum oven, Rotavapor®, air drying chamber, static bed dryer, fluid bed dryer, spray dryer and the like. In a preferred embodiment, the drying is made by static bed drying under vacuum at 45°±5° C.

Without being bound to any specific theory, the inventors of the present invention noted that surprisingly allopregnanolone 3α-trifluoroacetate is completely soluble in diisopropyl ether and TPPO is insoluble, while allopregnanolone 3α-trifluoroacetate crystallizes in high yields in isopropyl alcohol and TPPO is completely soluble.

Figure 5:
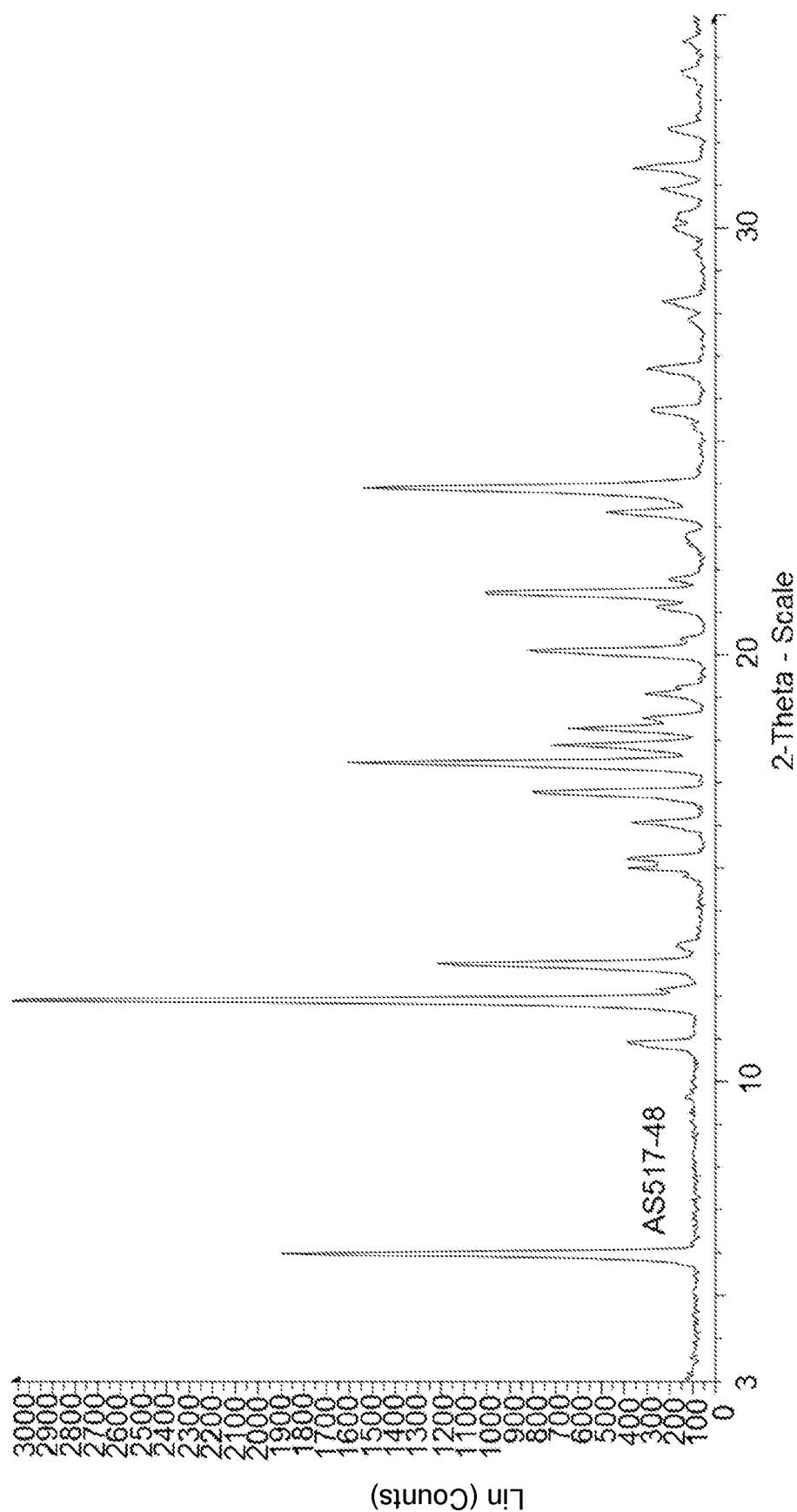
FIG. 5: XRPD spectrum of allopregnanolone 3α-trifluoroacetate obtained according to the invention.
Figure 6:
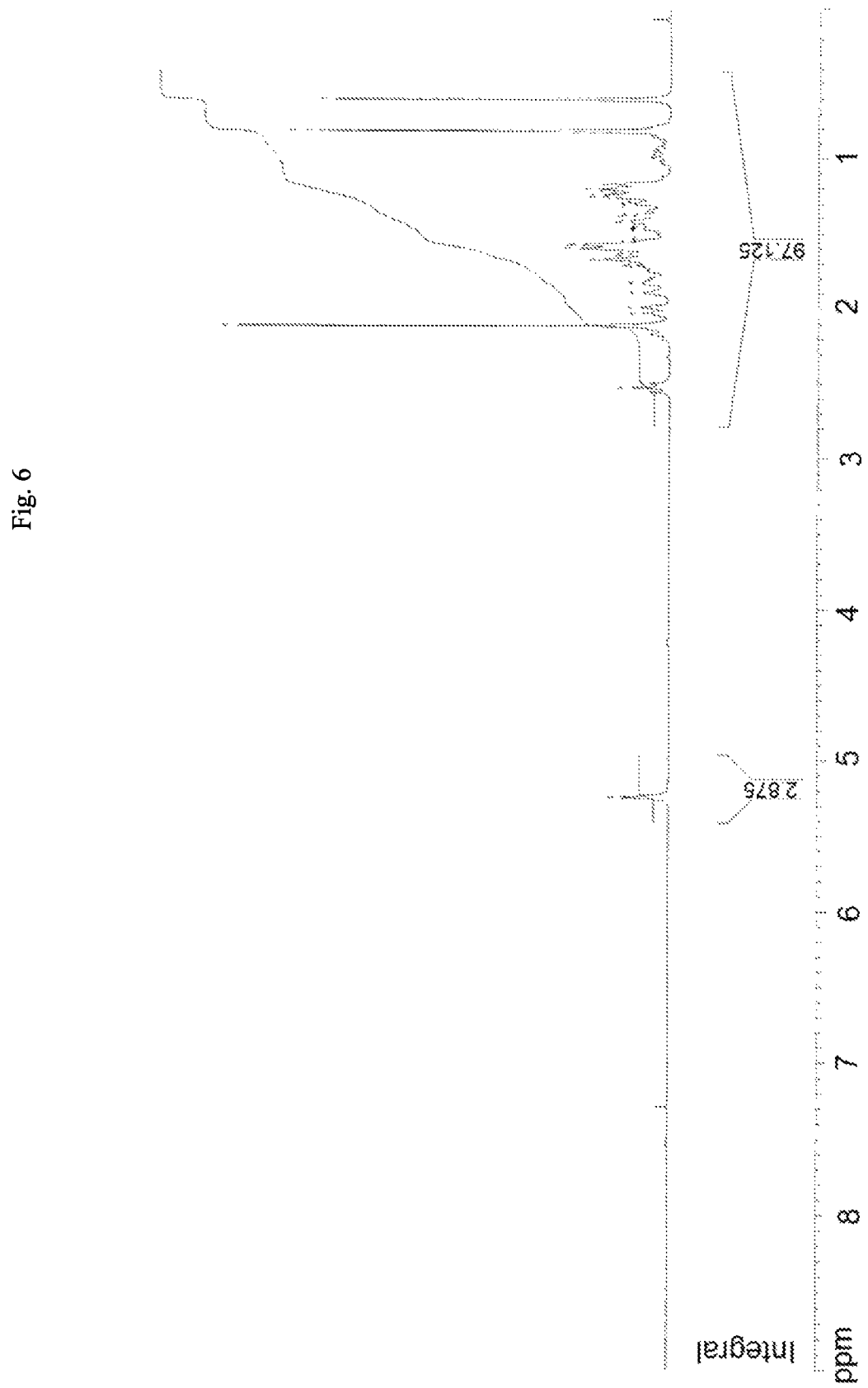
FIG. 6: ¹H NMR spectrum of allopregnanolone 3α-trifluoroacetate obtained according to the invention.
Figure 7:
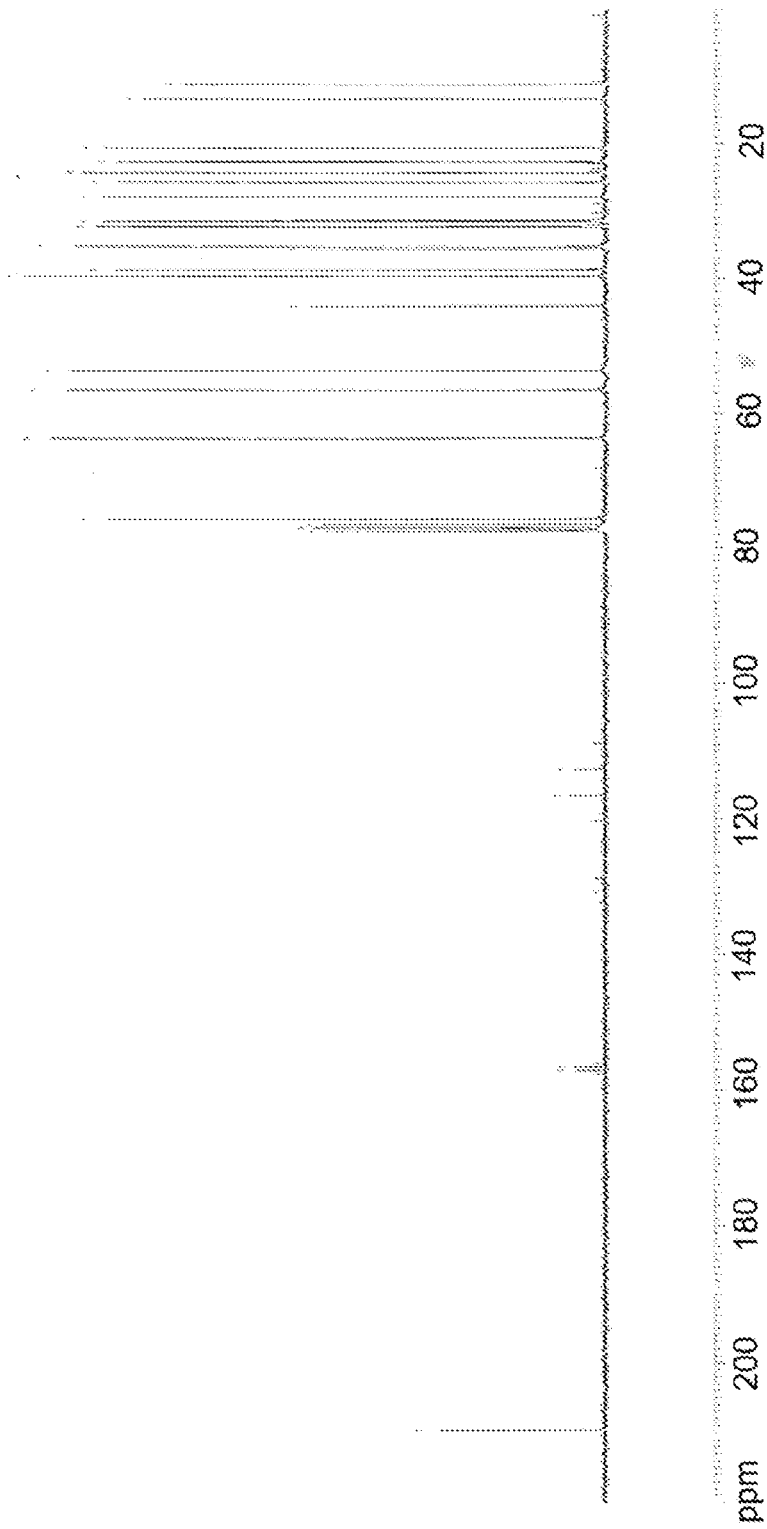
FIG. 7: ¹³C NMR spectrum of allopregnanolone 3α-trifluoroacetate obtained according to the invention.

Allopregnanolone 3α-trifluoroacetate, obtained according to the present invention, has been characterized by X-ray powder diffractometry (XRPD).
More particularly, allopregnanolone 3α-trifluoroacetate obtained according to the present invention shows, in the XRPD diffractogram (FIG. 5), at least three of the following characterizing peaks: 5.93, 11.91, 12.76, 16.79, 17.46, 17.89, 18.27, 20.11, 21.45 e 23.93±0.2 degrees 2-θ.

Allopregnanolone 3α-trifluoroacetate (II), isolated and purified according to the above described process, is then converted into allopregnanolone (I) by hydrolysis reaction in the presence of a base, preferably sodium hydroxide, still more preferably sodium hydroxide 28% w/v, in a suitable solvent, preferably methanol, and purified by crystallization from acetonitrile according to the first object of the invention.

Surprisingly, the resulting allopregnanolone has a purity of pharmaceutical grade and, more particularly, a TPPO content lower than 0.05 A % (see Table 2).

Even if the present invention has been described in its characterizing features, changes and equivalents which are evident to the skilled in the field are included in the present invention. Herein after, the present invention will be illustrated by some examples which have an illustrative purpose only and are not meant to limit the scope of the invention.

EXAMPLES

The melting point of allopregnanolone (I) obtained according to the process of the present invention was experimentally determined by melting point system Mettler MP90 model to give a range 174-175° C.

The optical rotation was determined by polarimeter Jasco P2000 and gave as a value $[\alpha]_D+96°$ (c=0.5, chloroform), wherein "c" is the concentration expressed as g/100 ml and chloroform is the solvent in which the measurement was made.

The $^1H$ and $^{13}C$ NMR were obtained by a spectrometer Bruker AV (300 MHz) at 25° C. observing $^1H$ and $^{13}C$ at 300.13 and 75.47 MHz, respectively. The chemical shifts are expressed as ppm related to tetramethylsilane and the spectra were obtained by dissolving the sample in $CDCl_3$.

The X-Ray Powder Diffraction (XRPD) spectra of allopregnanolone were performed with a diffractometer Bruker D5005, using Cu Kα radiation (λ=1.5418 Å), equipped with a scintillation detector and a curved graphite monochromator on the diffracted beam. The samples were mildly milled in an agate mortar to obtain a fine powder and to disintegrate eventual particle agglomerates. Data were collected at room temperature in a Silicon monocrystalline low-background

TABLE 2

| Allopregnanolone 3α-trifluoroacetate (g) | Allopregnanolone (g) | Allopregnanolone purity (%) | TPPO (A %) | Molar yield (%) |
|---|---|---|---|---|
| 5.1 | 3.3 | 99.79 | 0.05 | 89 |
| 13.8 | 8.8 | 99.70 | 0.024 | 86 |
| 11.3 | 7.6 | 99.76 | 0.031 | 89 |
| 17.3 | 9.2 | 99.81 | n.d. | 70 |

*n.d. = not detectable

Moreover, by correcting (dividing) A % by the suitable relative response factor k (wherein k=($A_{TPPO}$*[Allopregnanolone]/$A_{Allopregnanolone}$*[TPPO]=129), the value A %, representative of the residual TPPO concentration further decreases:

0.05%/129=0.0004%(<5 ppm)

In other words, TPPO is practically undetectable (<5 ppm) in allopregnanolone obtained according to the present invention.

Therefore, in a particularly preferred embodiment, the method for the purification of allopregnanolone of the present invention comprises:
the Mitsunobu reaction of isopregnanolone (III) to give allopregnanolone 3α-trifluoroacetate (II);
the filtration of a solution of allopregnanolone 3α-trifluoroacetate (II) in diisopropyl ether followed by its crystallization from isopropyl alcohol;
the hydrolysis reaction of allopregnanolone 3α-trifluoroacetate (II) to give allopregnanolone (I); and
the crystallization of allopregnanolone (I) from acetonitrile.

sample holder. Detection: 2θ degree, measurement of the angular range from 3° to 40°, step 0.03° and counting time of 4 s/step.

The X-Ray Powder Diffraction (XRPD) spectra of allopregnanolone 3α-trifluoroacetate were performed with a diffractometer Bruker D8, using Cu Kα radiation, equipped with a scintillation detector and a curved graphite monochromator on the diffracted beam. The samples were mildly milled in an agate mortar to obtain a fine powder and to disaggregate eventual particle agglomerates. Data were collected at room temperature in a Silicon monocrystalline low-background sample holder. Detection: 2θ degree, measurement of the angular range from 3° to 35° (2θ), step 0.04° and counting time of 2 s/step.

HPLC chromatograms were obtained by using Agilent 1100 Series and Agilent 1200 Series equipment and injecting 10 μL solution into a Kinetex XB C18; 150×4.6 mm; 5 μm column. The sample was eluted in gradient with a mobile phase composed of a mixture water/acetonitrile.

The compounds were finally analyzed by applying a wavelength equal to 210 nm.

Mass analyses were performed by using a Varian 500MS equipment in ESI+.

Example 1 (Comparative)

Crystallization Tests on Allopregnanolone Heavily Doped with TPPO (10% w/w)

The results are reported in Table 3:

TABLE 3

| TEST | SOLVENT | TPPO (% A) | Yield w/w |
|---|---|---|---|
| A | Acetonitrile | 16% | 90% |
| B | Aqueous ethanol | 40% | 37% |
| C | Acetone/ethyl acetate | 51% | 50% |
| D | Hexane/ethyl acetate | 52% | 63% |
| E | Ethyl acetate/ethanol | 63% | 9% |

Figure 8:
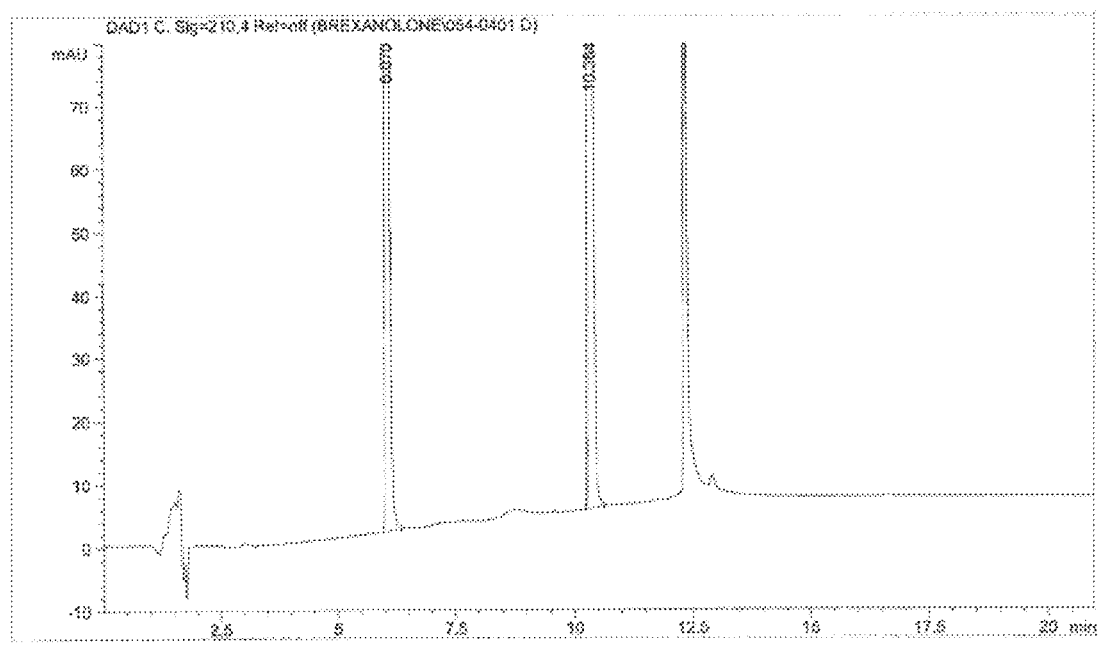
FIG. 8: HPLC chromatogram of allopregnanolone obtained by crystallization from aqueous ethanol.

Tests B-E result in allopregnanolone containing about 50% of TPPO impurity (rRT=0.59) as shown, for example, in FIG. 8.

The comparative example proves that acetonitrile, differing from all the other solvents or solvent mixtures, has the unexpected advantage to give allopregnanolone in higher yield and purity.

Example 2

Preparation of Allopregnanolone 3α-Trifluoroacetate 15 g of isopregnanolone and 150 mL (10V) of tetrahydrofuran were charged into a reaction flask at room temperature. The resultant suspension was stirred under inert atmosphere ($N_2$). Then, 26.51 mL of diethylazodicarboxylate (DEAD, 40% w in toluene) and 4.46 mL of trifluoroacetic acid were added at a temperature of about 5°±3° C. Subsequently, 15.3 g of triphenylphosphine were added, the reaction mixture was kept under stirring for about 10 minutes and the temperature was raised to 25°±2° C. Then, 8.4 g of sodium benzoate were added, and the mixture was kept under stirring for about 2 hours. The solvent was removed by distillation under vacuum up to 4V of residual solvent.

Subsequently, 90 mL (6V) of dichloromethane were added, the temperature was raised to about 30° C. and then 90 mL (6V) of water were added and the mixture was kept under stirring for 10±5 minutes. The phases were separated, and the collected organic phases were first treated with a saturated $NaHCO_3$ solution (90 mL, 6V), then with HCl 1N (90 mL, 6V) and, finally, with water (90 mL, 6V). The organic phases were concentrated by distillation under vacuum.

Example 3

Purification of Allopregnanolone 3α-Trifluoroacetate

Allopregnanolone 3α-trifluoroacetate was dissolved in 6V diisopropyl ether. The mixture was kept under stirring for about 30 minutes up to obtaining a precipitate. The precipitated solid was removed by filtration under vacuum. The filtrate was then concentrated and taken up with 6V isopropyl alcohol. The mixture was heated at 75° C. and kept under stirring for about 15 minutes. Subsequently, the mixture was cooled to 0° C. and kept under stirring for about 30 minutes. The precipitate was filtered and washed with 15 mL (1V) cold isopropyl alcohol. Then, the filtrate was dried under vacuum at room temperature to give allopregnanolone 3α-trifluoroacetate (7.5 g).

$^1$H NMR: 4.03 (1H, m, H-3 α); 2.53 (1H, m, H-17); 2.11 (3H, s, —$COCH_3$); 0.78 (3H, s, metil-19); 0.60 (3H, s, methyl-18); 1.00-2.20 (m, 22H).

$^{13}$C NMR: 11.2 ($CH_3$); 13.3 ($CH_3$); 20.7 ($CH_2$); 22.7 ($CH_2$); 24.2 ($CH_2$); 25.6 ($CH_2$); 27.9 ($CH_2$); 31.4 ($CH_3$); 31.5 ($CH_2$); 32.2 ($CH_2$); 32.4 ($CH_2$); 35.3 (CH); 35.6; 38.8 ($CH_2$); 39.7 (CH); 44.1; 53.7 (CH); 56.5 (CH); 63.6 (CH-17); 75.6 (C-3); 114.0 (q, $j_{C-F}$=285 Hz, —CF); 156.8 (q, $j_{C-F}$=41 Hz, —$COOCF_3$); 209.6 (C-20).

MS-positive ESI m/z 415.3 [M+H]$^+$.

Example 4

Preparation of Allopregnanolone 7.5 g allopregnanolone 3α-trifluoroacetate and 75 mL (10V) MeOH were charged into a reaction flask at room temperature. The resulting suspension was kept under stirring under inert atmosphere ($N_2$) and cooled to 5°±3° C. Subsequently, 3 g NaOH 28% w/v were added and the reaction mixture was kept under stirring for 10±5 minutes. The reaction mixture was treated by extraction from dichloromethane/water (6V/10V) while keeping under constant stirring for 10±5 minutes. The phases were separated and concentrated by distillation under vacuum.

Example 5

Purification of Allopregnanolone

Acetonitrile (10V) was charged into a reaction flask, the mixture was heated to 85°±5° C. and kept under stirring for about 15 minutes. Then, the mixture was cooled to 0° C. and kept under stirring for about 30 minutes. The precipitate was isolated by filtration under reduced pressure and washed with 7.5 mL (1V) cold acetonitrile. Finally, the filtrate was dried under vacuum at 45° C. for about 16 hours to give allopregnanolone (5.0 g).

$^1$H NMR: 4.03 (1H, m, H-3 α); 2.53 (1H, m, H-17); 2.11 (3H, s, —$COCH_3$); 1.57 (1H, s, exchange with D20, OH); 0.78 (3H, s, methyl-19); 0.60 (3H, s, methyl-18); 1.00-2.20 (m, 22H).

$^{13}$C NMR: 11.1 ($CH_3$); 13.3 ($CH_3$); 20.7 ($CH_2$); 22.6 ($CH_2$); 24.2 ($CH_2$); 28.3 ($CH_2$); 28.8 ($CH_2$); 31.4 ($CH_3$); 31.8 ($CH_2$); 32.1 ($CH_2$); 35.3 (CH); 35.7 ($CH_2$); 36.0; 38.9 (CH); 38.9 ($CH_2$); 44.1; 54.1 (CH); 56.7 (CH); 63.7 (CH-17); 66.3 (CH-3); 209.6 (C-20).

MS-positive ESI m/z 319.2 [M+H]$^+$; 301.1 [M–$H_2$O+H]$^+$

The invention claimed is:

1. A method for the purification of allopregnanolone of formula (I)

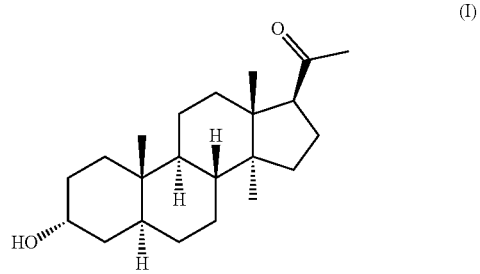

comprising crystallizing allopregnanolone from acetonitrile.

2. The method according to claim 1, further comprising recrystallizing the allopregnanolone from acetonitrile.

3. The method according to claim 1, further comprising preparing the allopregnanolone by Mitsunobu reaction of a compound of formula

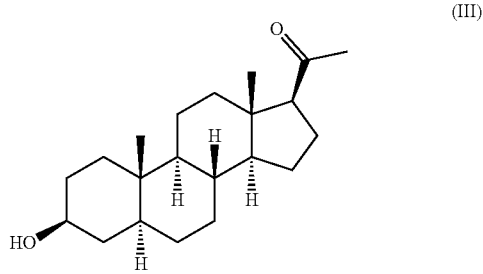

(III)

to give a compound of formula

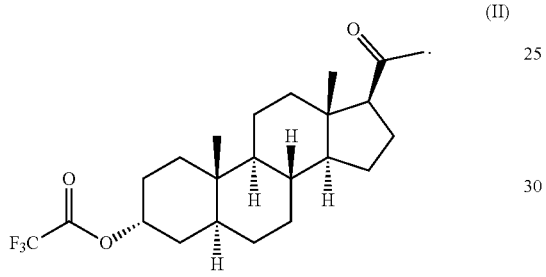

(II)

4. The method according to claim 3, wherein the Mitsunobu reaction occurs by reacting the compound of formula (III) with trifluoroacetic acid in the presence of an azodicarboxylate, triphenylphosphine and sodium benzoate, in a reaction solvent.

5. The method according to claim 4, wherein the solvent is tetrahydrofuran.

6. The method according to claim 4, wherein the azodicarboxylate is selected from the group consisting of diethylazodicarboxylate, diisopropyl azodicarboxylate and di-tent-butyl azodicarboxylate.

7. The method according to claim 6, wherein the azodicarboxylate is diethylazodicarboxylate.

8. The method according to claim 3, further comprising filtering a solution of the compound of formula (II) in diisopropyl ether and the recrystallization thereof from isopropyl alcohol.

9. The method according to claim 3, wherein said preparation further comprises the conversion of the compound of formula (II) into the compound of formula (I) by hydrolysis reaction in the presence of a base, and in a solvent.

10. The method according to claim 9, wherein the base is sodium hydroxide.

11. The method according to claim 9, wherein the solvent is methanol.

12. Allopregnanolone obtained according to claim 1, having, in the XRPD diffractogram, at least three of the following characterising peaks: 7.25, 8.87, 9.58, 11.43, 14.41, 14.77, 15.73, 17.78, 18.16, 18.60 and 19.98 ±0.2 2-θ degrees.

13. The compound of formula (II):

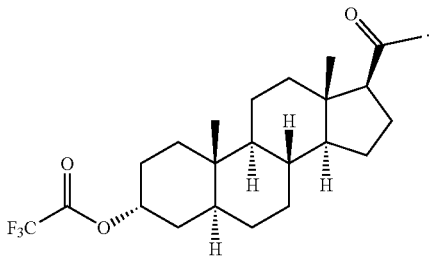

* * * * *